United States Patent
Stamm et al.

(10) Patent No.: US 11,099,169 B2
(45) Date of Patent: Aug. 24, 2021

(54) DUAL PORE—CONTROL AND SENSOR DEVICE

(71) Applicant: Nooma Bio, Inc., Santa Cruz, CA (US)

(72) Inventors: Reto Stamm, Half Moon Bay, CA (US); Michael Summers, Santa Cruz, CA (US); Eric Thorne, Santa Cruz, CA (US); William B. Dunbar, Santa Cruz, CA (US)

(73) Assignee: Nooma Bio, Inc., Santa Cruz, CA (US)

( * ) Notice: Subject to any disclaimer, the term of this patent is extended or adjusted under 35 U.S.C. 154(b) by 316 days.

(21) Appl. No.: 16/009,007

(22) Filed: Jun. 14, 2018

(65) Prior Publication Data

US 2018/0372713 A1    Dec. 27, 2018

Related U.S. Application Data (60) Provisional application No. 62/523,228, filed on Jun. 21, 2017.

(51) Int. Cl.
*G01N 33/487* (2006.01)
*C12Q 1/6869* (2018.01)
(Continued)

(52) U.S. Cl.
CPC ..... *G01N 33/48721* (2013.01); *C12Q 1/6869* (2013.01); *G01N 27/44743* (2013.01);
(Continued)

(58) Field of Classification Search
CPC ....... G01N 33/48721; G01N 27/44743; G01N 27/44791; C12Q 1/6869; C12Q 2565/631; B82Y 15/00; B82Y 30/00
See application file for complete search history.

(56) References Cited

U.S. PATENT DOCUMENTS 6,740,518 B1    5/2004 Duong et al.
8,961,763 B2    2/2015 Dunbar et al.
(Continued)

FOREIGN PATENT DOCUMENTS

EP            1 912 062 A1    4/2008
WO    WO 2013/014451 A1    1/2013
WO    WO 2018/093976 A1    5/2018

OTHER PUBLICATIONS

PCT International Search Report and Written Opinion, PCT Application No. PCT/US2018/037634, dated Sep. 6, 2018, thirteen pages.
(Continued)

*Primary Examiner* — J. Christopher Ball
(74) *Attorney, Agent, or Firm* — Fenwick & West LLP (57) ABSTRACT

Two-pore devices and method for sequencing are described. A two-pore device can include first chamber, a second chamber, and a third chamber, wherein the first chamber is in communication with the second chamber through a first nanopore, and wherein the second chamber is in communication with the third chamber through a second nanopore. The device can also include sensing circuitry for measuring electrical signals associated with a target at a nanopore, and control circuitry for controlling motion of the target at a nanopore. The device can include and/or switch between sensing and control modes for each of the first nanopore and the second nanopore. Sequencing methods can implement a two-pore device in relation to translocation of a target through one or more nanopores, switching between sensing and control modes as appropriate, and measuring aspects of the target using in sensing modes.

20 Claims, 7 Drawing Sheets

(51) Int. Cl.
*G01N 27/447* (2006.01)
*B82Y 30/00* (2011.01)
*B82Y 15/00* (2011.01)

(52) U.S. Cl.
CPC ........ *G01N 27/44791* (2013.01); *B82Y 15/00* (2013.01); *B82Y 30/00* (2013.01)

(56) References Cited

U.S. PATENT DOCUMENTS

| | | | |
|---|---|---|---|
| 2011/0031389 A1* | 2/2011 | Reed | G01N 33/48721 250/282 |
| 2014/0318964 A1 | 10/2014 | Dunbar et al. | |
| 2015/0160160 A1 | 6/2015 | Dunbar et al. | |
| 2018/0155768 A1 | 6/2018 | Cohen et al. | |

OTHER PUBLICATIONS

Garalde, D.R., et al., "Modeling the Biological Nanopore Instrument for Biomolecular State Estimation." IEEE Transactions on Control Systems Technology, Nov. 2013, vol. 21, No. 6, pp. 2038-2051.
Kim, J., et al., "A patch-clamp ASIC for nanopore-based DNA analysis," IEEE transactions on biomedical circuits and systems, Jun. 2013, vol. 7, No. 3, pp. 285-295.
Lam, E., et al., "Genome mapping on nanochannel arrays for structural variation analysis," Nature Biotechnology, Aug. 2012, pp. 771-777, vol. 30, No. 8.
Lathrop, D., et al., "Monitoring the Escape of DNA from a Nanopore Using an Alternating Current Signal," Am Chem Soc., Feb. 17, 2010, pp. 1878-1885, vol. 132, No. 6.
O'Donnell, C., et al., "Error Analysis of idealized nanopore sequencing," Fast Track, Electrophoresis, 2013, pp. 2137-2144, vol. 34.
Skogestad, S., et al., "Multivariable feedback control: analysis and design," Second Edition, Aug. 29, 2001, New York: Wiley, 585 Pages.

* cited by examiner

DUAL PORE—CONTROL AND SENSOR DEVICE

CROSS REFERENCE TO RELATED APPLICATIONS

This application claims the benefit of U.S. Provisional Application Ser. No. 62/523,228 filed 21 Jun. 2017, which is incorporated in its entirety herein by this reference.

BACKGROUND

A nanopore is a nano-scale conduit that forms naturally as a protein channel in a lipid membrane (a biological pore), or is engineered by drilling or etching the opening in a solid-state substrate (a solid-state pore). When such a nanopore is incorporated into a nanodevice comprising two chambers that are separated by the nanopore, a sensing device, such as a patch clamp or voltage clamp system, can be used to apply a trans-membrane voltage and measure ionic current through the pore.

Nanopores offer great promise for inexpensive whole genome DNA sequencing. Two obstacles to nanopore sequencing: (1) the lack of sensitivity sufficient to accurately determine the identity of each nucleotide in a nucleic acid for de novo sequencing (the lack of single-nucleotide sensitivity), and (2) the ability to regulate and control the delivery rate of each nucleotide unit through the nanopore during sensing. These two obstacles are often inter-related as the inability to regulate delivery rates is one of the underlying problems that can be associated with the lack of single-nucleotide sensitivity. Stated another way, if the DNA is traversing past the sensor too rapidly, then the sensor's function can be compromised. There is no existing method for addressing obstacle 2 that does not involve the use of enzymes or optics, both of which work only in specialized nanopore techniques and which incur higher complexity and cost compared to electrical methods.

BRIEF DESCRIPTION OF DRAWINGS

The disclosed embodiments have advantages and features that will be more readily apparent from the detailed description, the appended claims, and the accompanying figures (or drawings). A brief introduction of the figures is below.

DETAILED DESCRIPTION

Overview

The present disclosure describes a two-nanopore device in which each of the two nanopores are incorporated within a switchable two circuit option. A first circuitry that incorporates a nanopore, hereafter referred to as the sensor circuitry, comprises a sensing voltage clamp or patch clamp amplifier circuit. When the first circuitry that incorporates a nanopore is used, the nanopore serves as an "ionic current sensing" nanopore. The second circuitry, hereafter referred to as the control circuitry, comprises customized circuitry that controls the magnitude and direction of the field forces across a nanopore incorporated within the second circuitry. In various embodiments, the control circuitry comprises a phase-locked loop (PLL) or some other periodic voltage-control waveform. The control circuitry also has access to information from the first circuitry (e.g., a measured current) that can be used for feedback voltage-control. In this configuration, a sensing circuitry is applied to a first nanopore while a control circuitry, which is designed for optimal trans-pore voltage-control, is applied to a second nanopore. Switching between the two circuit types can be done at any time. In other words, a sensor circuitry can be applied to the second nanopore while a control circuitry is applied to the first nanopore. Generally, a control circuitry at one nanopore is used to affect motion of a molecule through the other nanopore, thereby enabling multiple re-readings of the molecule using the sensing circuitry of the opposite nanopore. In various embodiments, the combination of the control circuitry and sensing circuitry operated at two different nanopores can be used to address obstacle 2 described above, by slowing the molecule as it translocates through a nanopore during controlled delivery and sensing.

An example two nanopore device can be used to capture individual molecules into two nanopores at one time, and using the sensing circuit to measure the translocation of the molecule through one nanopore. Such embodiments describing a two-pore device can comprise: a first membrane layer comprising a first nanopore fluidically connecting a first chamber with a second chamber; and a second membrane layer comprising a second nanopore fluidically connecting the second chamber to a third chamber, wherein the first nanopore is connected within a sensor circuitry that applies a constant voltage across the first nanopore and measures current through the first nanopore, and wherein the second nanopore is connected within a control circuitry that applies a dynamic voltage across the second nanopore. In an alternative embodiment, the first pore is connected to a control circuitry and the second pore is connected to a sensing circuitry.

Referring to the first circuitry of each nanopore, the circuitry incorporated can be one of a patch clamp or voltage clamp amplifier. The TIA of the first circuitry provides a constant field force across the nanopore when the voltage is set constant, with the current measured through the nanopore acting as the sensing signal that detects the presence and passage of a molecule such as a DNA, RNA, proteins, and any combination of these molecules (macro-molecules). In this respect, the TIA (patch clamp, voltage clamp) is an example of a "sensing circuit" circuit used in nanopore assays. The voltage is set constant during sensing, and thus provides no direct control over any passing molecule in the nanopore, but applies a field force that acts on the molecule before, during, and after nanopore transit in the range of field-force influence. In various embodiments, the patch clamp is designed for optimal sensing, not as a voltage actuation mechanism.

Referring to the second circuitry of each nanopore, the control circuitry option, which is optimized for DNA motion control, can be implemented at each nanopore and can use the measurement from the first circuit (e.g., measured current) as a feedback signal for feedback motion control of the captured molecule. In various embodiments, the voltage applied by the control circuitry is an oscillatory voltage signal that is dependent on the feedback signal from the first circuit. For example, the voltage applied by the control circuitry can be modulated, when desired, as a function of feedback data gathered by the sensor circuitry. Data includes frequency, amplitude, phase, event duration, quantity, and other comparative relations pertaining to a translocation event or sequence of translocation events, or patterns within translocation events (e.g., sequence-specific signatures that register as changes in signal depth within the event). As an example, in various embodiments, the control circuitry applies the dynamic voltage using a direct current-biased alternating current signal source. The dynamic voltage can be applied by the control circuitry with a wide frequency range, potentially between 0.001 Hz and 100 MHz and a varying amplitude range between 0.001V and 10 V. In other embodiments, the voltages and frequencies applied could be in other ranges.

In various embodiments, the measured current detected by a sensing circuit is affected by changes in the voltage applied by the control circuit, e.g., since voltage changes excite any shared capacitance between the pores, including the capacitance of the membranes comprising each pore. As such, filters and estimators, including an extended Kalman filter implementation, can be designed or co-designed to estimate molecule-induced changes in the current that are superimposed on the sensing signal.

Also provided herein are methods for determining the sequence of a molecule such as one of a charged polypeptide, polynucleotide, phospholipid, polysaccharide, and polyketide, or another type of molecule. The method of sequencing a molecule comprises: a) loading a sample comprising a polynucleotide in one of the first or second chamber of the device of any of the above embodiments, wherein the device is connected to a sensor circuitry, such as a voltage clamp or patch clamp system, for providing a first voltage across a first nanopore located between the first chamber and the middle layer, and a second voltage across a second nanopore located between the middle layer and the second chamber; (b) setting an initial first voltage and an initial second voltage so that the polynucleotide moves through the chambers, thereby locating the polynucleotide across both the first and second nanopores; (c) adjusting the first voltage and the second voltage, wherein the two voltages are different in magnitude, under controlled conditions, so that the polynucleotide moves through the first and second nanopores in one direction and in a controlled manner; (d) switching from a sensing circuitry to a control circuitry at the first pore or the second pore, and employing the control circuitry at said pore for enhanced controlled delivery of the polynucleotide through the other pore still using the sensing circuitry (the "sensing nanopore"); and (e) identifying each nucleotide of the polynucleotide that passes through the sensing nanopore.

Example Nanopore Device

Figure 1:
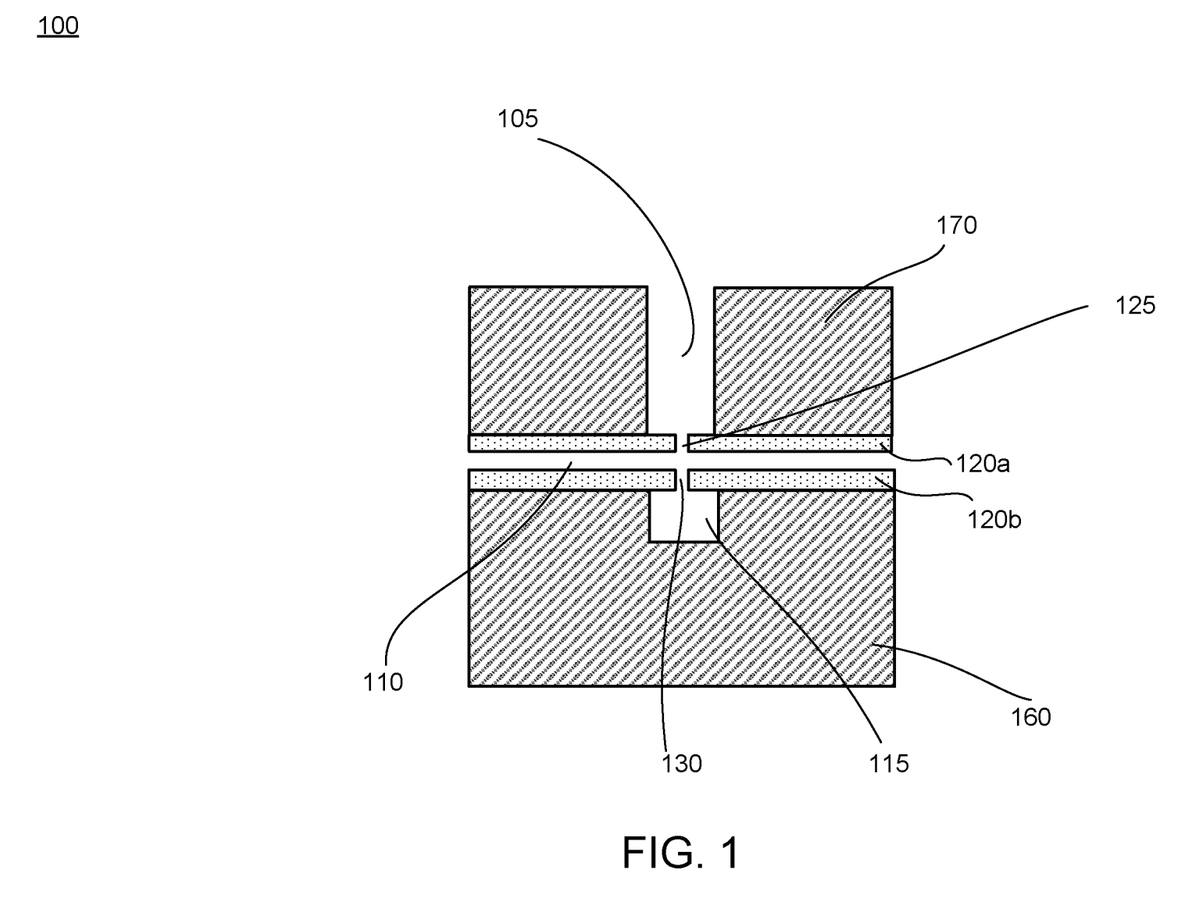
FIG. 1 depicts an example nanopore device with two nanopores, in accordance with one embodiment.

In various embodiments, an example nanopore device 100 for employing the two-nanopore, one-sensor configuration is a multiple chamber, two-pore device. With reference to FIG. 1, the example nanopore device 100 includes a first chamber 105, a second chamber 110, and a third chamber 115. In various embodiments, the first chamber 105 is located within a cover 170 that may be composed of an insulating material such as glass. The third chamber 115 is generated on the surface of an insulating layer 160 composed of an insulating material such as glass. The chambers are separated by two membranes (120a and 120b) that, in various embodiments, are composed of a material selected from several options. In a solid-state fabrication process, the membrane material can be silicon nitride, silicon dioxide, aluminum oxide, graphene, any combinations of these, or any other solid-state material known in the art. An alternative would be a polymer membrane with a biological nanopore inserted. Each membrane layer 120a and 120b includes a separate nanopore, hereafter referred to as a first nanopore 125 and a second nanopore 130. The first nanopore 125 may be a solid-state nanopore, a biological nanopore, or a Field Effect Nanopore Transistor (FENT). The second nanopore 130 may be any of those systems, or an even larger micropore (μm scale). The first nanopore 125 is in fluidic connection with the first chamber 105 and the second nanopore 130 is in fluidic connection with the third chamber 115.

The depiction of the first, second, and third chambers FIG. 1 is shown as one example and does not indicate that, for instance, the first chamber is placed above the second or third chamber, or vice versa. The two nanopores 125 and 130 can be arranged in any position so long as they allow fluid communication between the chambers. Still, in one aspect, the nanopores are aligned as illustrated in FIG. 1.

In various embodiments, an example nanopore device 100 for employing a two-nanopore, one-sensor configuration is a two chamber, two-pore device. As an example, a two chamber, two-pore device can include a first chamber and second chamber that are each in fluid communication with a first 125 and second nanopore 130, respectively. A plurality of layers can separate the two chambers. For example, the plurality of layers comprise: a first layer; a second layer; and a conductive middle layer disposed between the first and second layers. In this two chamber, two-pore device, the first nanopore 125 and second nanopore 130 may be connected to one another through a channel that is located within the conductive middle layer. A channel refers to any fluid path that enables fluid flow between the first nanopore 125 and second nanopore 130.

Example Two-pore, One Sensor

Figure 2A:
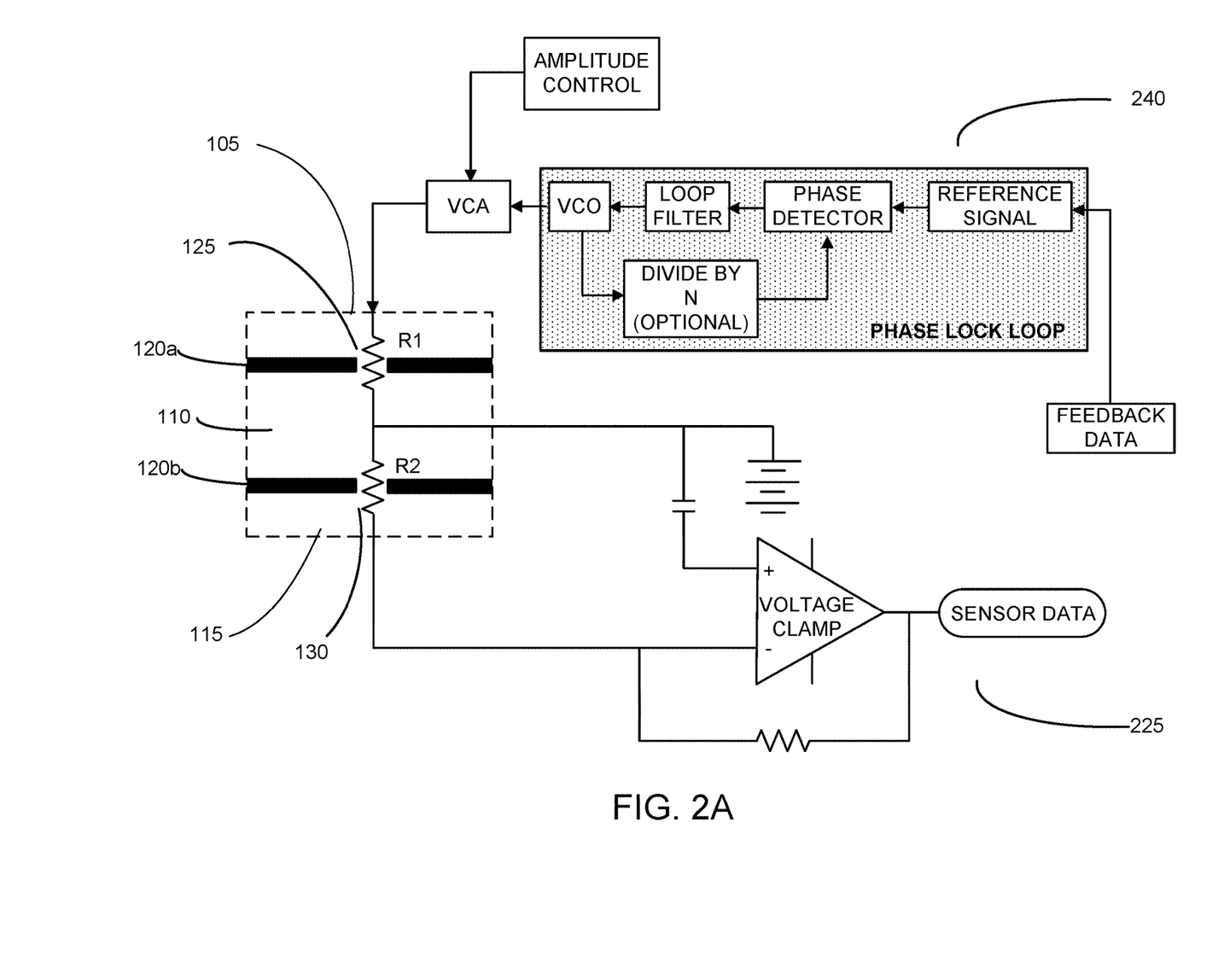
FIG. 2A-B each depicts example circuitry incorporating the two nanopores of an example nanopore device, in accordance with two embodiments.
Figure 2B:
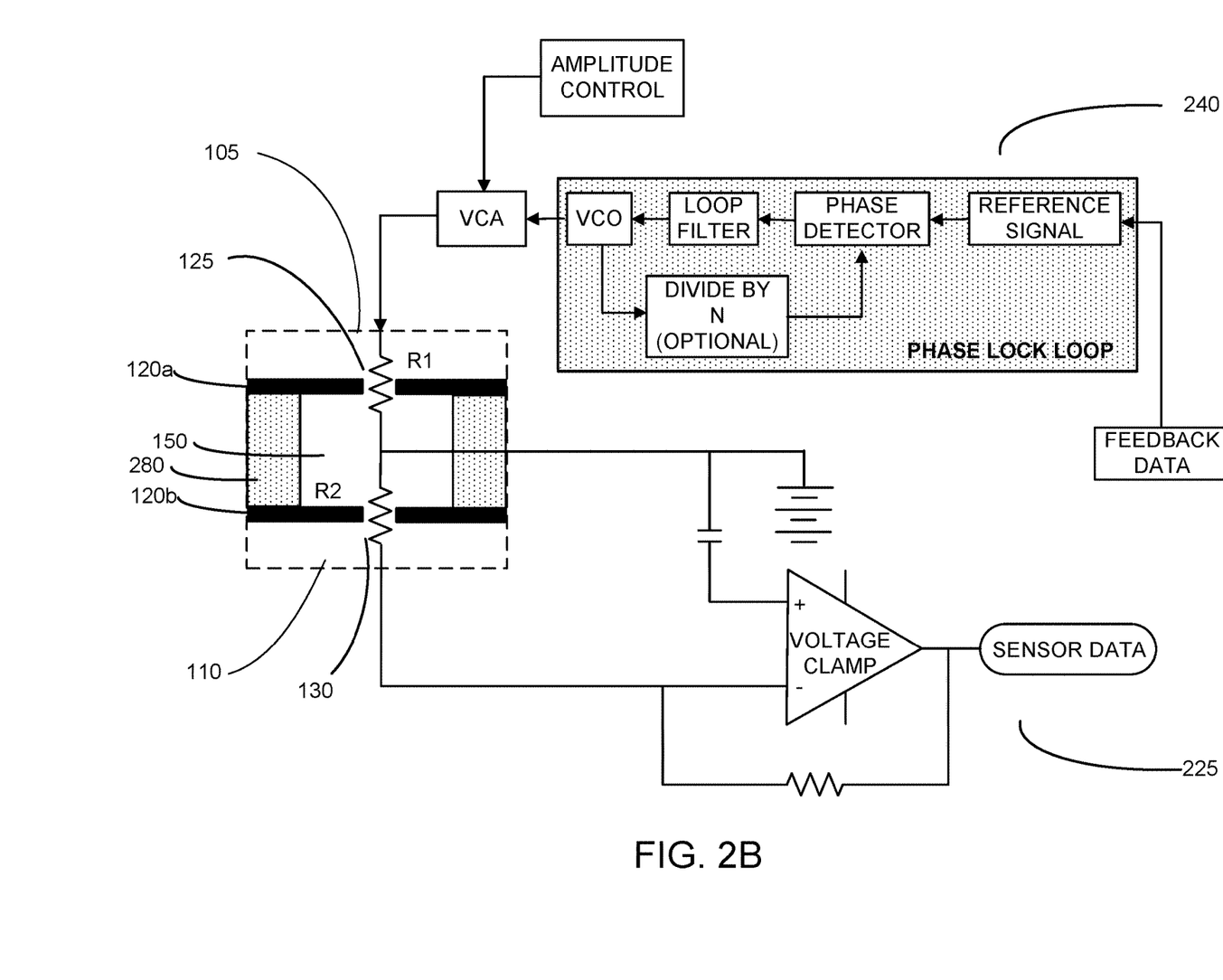

In the present disclosure, a sensor circuitry including a TIA, such as a voltage clamp or patch clamp, is used for applying a constant voltage and detecting ionic changes across a nanopore. Additionally, a control circuitry is used at a nanopore to control movement of a molecule. FIG. 2A-B each depicts example circuitry incorporating the first 125 and second nanopores 130 of an example nanopore device, in accordance with two embodiments.

Specifically, FIG. 2A depicts the circuitry of an example multiple chamber, two-pore device 100 (see FIG. 1) that includes a first chamber 105, a second chamber 110, and a third chamber 115. In this embodiment, sensing and controlling of a molecule can occur while at least a portion of the molecule resides within the second chamber 110. Additionally, FIG. 2B depicts a two chamber, two-pore device 100 that includes a first chamber 105, second chamber 110, and a channel 150 located between the first nanopore 125 and second nanopore 130. In this embodiment, sensing and controlling of a molecule can occur while at least a portion of the molecule resides within the channel 150.

Although this embodiment depicts two nanopores, the circuitry design can be applied to more than two nanopores. Additionally, as depicted in the embodiments shown in FIG. 2A and FIG. 2B, the example circuitry includes a sensor circuitry 225 that incorporates the first nanopore 125 and a control circuitry 240 that incorporates the second nanopore 130. In other embodiments, the sensor circuitry 225 may instead incorporate the second nanopore 130 whereas the control circuitry 240 incorporates the first nanopore 125. In further embodiments, each of the first nanopore 125 and second nanopore 130 may be incorporated within a circuitry that is switchable between a sensor circuitry and a control circuitry. Therefore, sensing and controlling a molecule can be performed at both nanopores 125 and 130.

Sensor Circuitry

As shown in FIGS. 2A and 2B, the sensor circuitry 225 may be one of a voltage clamp or a patch clamp that 1) applies a static voltage across the second nanopore 130 and 2) captures sensor data as a molecule passes through the second nanopore 130.

The nanopore device can include a common voltage for the first 125 and second nanopores 130 the sensor circuitry 225. For example, in the embodiment shown in FIG. 2A, the middle chamber 110 of the nanopore device can serve as the common voltage for the first 125 and second nanopores 130. In the embodiment shown in FIG. 2B, the two chamber, two-pore device may include a middle conductive layer 280 that can serve as the common voltage. In various embodiments, the electrical connection of the middle chamber 110 is achieved through a metallic electrode located within the two membrane layers 120a and 120b between the two nanopores 125 and 130. In some embodiments, the electrical connection is achieved through a physical connection to a metallic electrode external to the middle chamber 110. The common voltage potential can refer to a reference voltage set by an external system. In some embodiments, the common voltage is a common ground for the first nanopore 125 and second nanopore 130.

The sensor circuitry 225 can be further configured to enable the capture of sensor data corresponding to molecules (e.g., polynucleotide such as DNA) that translocate across the second nanopore 130. In one aspect, the sensor circuitry 225 further includes one or more sensors to capture the sensor data. In one aspect, the sensor includes a pair of electrodes placed at either side of the second nanopore 130 to measure an ionic current across the second nanopore 130 when a molecule, in particular a polynucleotide, translocates through.

The measured ionic current across the second nanopore 130 is dependent on the geometry of the second nanopore 130. For example, the second nanopore 130 possesses a resistance R2 within the sensor circuitry 225. The resistance R2 is dependent on the geometry (e.g., diameter) of the second nanopore 130. The resistance R2 represents the dynamic pore conductance that is measured by the sensor circuitry 225 to sense the translocation of molecules through the second nanopore 130.

In some aspects, the sensor is configured to form a tunnel gap at the second nanopore 130 that allows the detection of a molecule when translocating through the tunnel gap. When the molecule moves through the tunnel gap, the sensor is then able to identify the individual components (e.g., nucleotides) of the molecule. In some embodiments, the sensor is functionalized with reagents that form distinct non-covalent bonds with each nucleotide base. Tunnel sensing with a functionalized sensor is termed "recognition tunneling." Using a Scanning Tunneling Microscope (STM) with recognition tunneling, a DNA base flanked by other bases in a short DNA oligomer can be identified. Recognition tunneling can also provide a "universal reader" designed to hydrogen-bond in a unique orientation to each of the four DNA bases (A, C, G, T) and also to the base 5-methyl-cytosine (mC) which is naturally occurring due to epigenetic modifications.

Control Circuitry

The control circuitry controls the motion of a molecule (e.g., DNA polynucleotide, protein, and the like) that is captured into both of the first and second nanopores at the same time. Generally, the control circuitry applies a directional field force that opposes the field force arising from the voltage applied by the sensor circuitry at the second nanopore 130. The control circuitry does not incorporate a voltage clamp or patch clamp circuit. Instead, the control circuitry utilizes voltage-control elements. These voltage-control elements provide performance for control that surpasses what is possible with a voltage clamp or patch clamp amplifier circuitry (e.g., the sensor circuitry). In particular, such control elements can provide a wide variety of waveforms that can be specifically configured to precisely control the motion of a molecule within the two nanopores. Furthermore, the current measurements detected by the sensor circuitry at the second nanopore 130 can serve as feedback for the control elements of the control circuitry in real-time.

Referring to the control circuitry 240 in either FIG. 2A or 2B, it can include various ways to control both current and voltage. Control methods can include, but are not limited to, a voltage-controlled amplifier (VCA), digital control amplifier (DCA), pulse width modulator (PWM), an amplitude control, or a phase loop lock (PLL) working separately or in combination. Generally, the control circuitry 240 1) applies a dynamic voltage across the first nanopore 125 and 2) controls the movement of a molecule through the second nanopore 130. The control circuitry 240 applies a dynamic voltage across the first nanopore 125. The applied dynamic voltage imparts a force upon the molecule that opposes the force imparted by the static force generated by the sensor circuitry 225, with an opposing force strength that is less than the static force strength for molecule motion toward the sensing pore, or with an opposing force strength that is greater than the static force strength for molecule motion toward the controlling pore. Therefore, varying the dynamic voltage enables the control over the direction of motion of the molecule as well as the rate of motion (e.g., velocity) of the molecule through the second nanopore 130.

The control circuitry can also be configured to provide an electric field associated with a direct current (DC) source or an alternating current (AC) source. In one application, application of a driving force, by way of an AC electric field having an associated frequency can be used to control position, velocity, and/or acceleration of a target at, through, or between one or more of the nanopores of the system.

The control circuitry can receive feedback data that can be used to apply the dynamic voltage. As an example, the feedback data can be detected by the sensor circuitry 225 (e.g., measured current through a nanopore incorporated in the sensor circuitry 225). In one embodiment, the feedback data may be the frequency (e.g., period) in which a molecule repeatedly passes back and forth through the second nanopore 130, which is derived from the sensor data captured by the sensor circuitry 225. Therefore, the applied dynamic voltage can ensure that the molecule continues to pass back and forth through the second nanopore 130 incorporated by the sensing circuitry 225.

To generate the dynamic voltage, the PLL of the control circuitry 240 receives the feedback data, which can correspond to a measured current detected by the sensing circuitry 225. The measured current can be filtered and compared to a reference signal to generate an error signal (e.g., difference between reference signal and frequency data). Additionally, other filtered versions of the error signal can be used to adjust the control voltage signal in real-time. The first and higher order derivatives of the error signal, and/or integral(s) of the error signal, in addition to a proportional error term, could be used in the feedback calculation. The reference signal could be known a priori, based on data gathering and learning done in prior experiments, or it could be generated during the experiment through an adaptive or real-time learning process or a combination thereof.

In various embodiments, if the molecule is a DNA molecule, an example reference signal can be attenuation pulses within the DNA signal that match known sequence-specific payloads bound at known sites on a double stranded DNA (dsDNA) scaffold, with each payload generating a pulse as it passes through a nanopore, relative to the dsDNA signal level without a payload. In that example, the reference pulse frequency desired could correspond to a known DNA rate through a nanopore. Another reference signal could be based on a desired rate of change of a measured signal in the feedback data, i.e., to either speed up or slow down the detection of step changing events within the measured signal, whether known a priori to exist or not. Another reference signal is based on a desired phase of frequency data, which can be used in a phase-lock loop controller circuit.

The control circuitry 240 may include a feedback controller that is configured to stabilize the control voltage signal relative to that reference signal, in either feedforward or feedback directions. In various embodiments, the feedback and feedforward control system could be designed and implemented with a sufficiently detailed model of the total system, e.g., identified using system identification tools. The feedback drives the error to zero (e.g., so that the measured signal will match a defined reference signal). Even in the presence of uncertainty, feedforward aids in reference tracking and disturbance rejection, to improve the total system performance. The feedback or feedforward signal can be designed in either a frequency domain (e.g., frequency) or a time domain (e.g., period).

In various embodiments, such as those depicted in FIGS. 2A and 2B, the reference signal is processed to determine the phase of the feedback data. The output voltage of the phase detector is used to control the voltage-controlled oscillator (VCO) such that the phase difference between the phase of the voltage signal outputted by the VCO and the phase of the reference signal is held constant, thereby making it a negative feedback system. In various embodiments, as depicted in FIG. 2A/2B, the feedback loop incorporates a fractional-N synthesizer such as a divide-by-N function. This ensures that the output from the VCO is a rational multiple of the reference frequency and can enable comparisons at specified frequency resolutions.

The voltage output from the PLL is amplified by the voltage-controlled amplifier (VCA) based on an amplitude control. The VCA provides control of peak voltages applied across the first nanopore 125. The first nanopore 125 possesses a resistance R1 that is dependent on the geometry (e.g., diameter) of the first nanopore 125. The resistance R1 represents the dynamic pore conductance that acts as the load for the PLL and VCA output.

Altogether, the control circuitry 240 incorporating the first nanopore 125 serves as an electromagnetic force circuit. In other words, the voltage applied across the first nanopore 125 creates an electromagnetic field force which interacts with a molecule located between the membrane layers 120a and 120b in the middle chamber 110. The applied force directs the molecule in either direction (e.g., towards the first nanopore 125 and away from the second nanopore 130 or towards the second nanopore 130 and away from the first nanopore 125), through the selection of the magnitude of the applied voltage across the first nanopore 125 relative to the magnitude of the applied voltage across the second nanopore 130. During control, the voltage polarities are set to pull DNA away from the middle chamber between the pores, and the voltage magnitude of the control circuitry is adjusted relative to the voltage applied by the sensing circuitry to achieve net motion of DNA in either direction. Therefore, the application of a dynamic voltage that alters the electromagnetic field force that interacts with the molecule enables the repeated back and forth movement of the molecule through the second nanopore 130.

In various embodiments, the control circuitry 240 employs a periodic voltage-control mechanism across the first nanopore 125 using a direct current (DC)-biased AC signal source. This signal source can tune at least two parameters that enable the dynamic adjustment of the applied voltage and the resulting electric field/force at the first nanopore 125:

1) The amplitude (or gain) of the signal source, and
2) The period (or frequency) of the signal source.

Other parameters of the input voltage signal such as duty cycle, wave shape (sinusoidal, square, sawtooth), and stop periods may be applied by the signal source as well. In various embodiments, the signal source may be a single device such as the AD9102 Digital-to-Analog Converter and Waveform Generator. Such a device can easily produce a wide range (e.g., frequency range of 0.001 Hz to 100 MHz) of waveforms while controlling: gain, period, duty cycle, and wave shape. In some embodiments, the wide frequency range of waveforms of an input voltage signal can be achieved by employing a variable frequency output phase lock loop (PLL) (or other clock generator), as depicted in FIG. 2A/2B. The PLL can be placed in series with a variable gain amplifier. PLLs can be either fixed frequency or variable with certain ranges (e.g., 8 kHz-250 MHz see: IDT 8T49N1012). In various embodiments, multiple PLLs can be included in the control circuitry 240 in series to achieve wider frequency ranges.

Switchable Sensing and Control Circuitry

Figure 3:
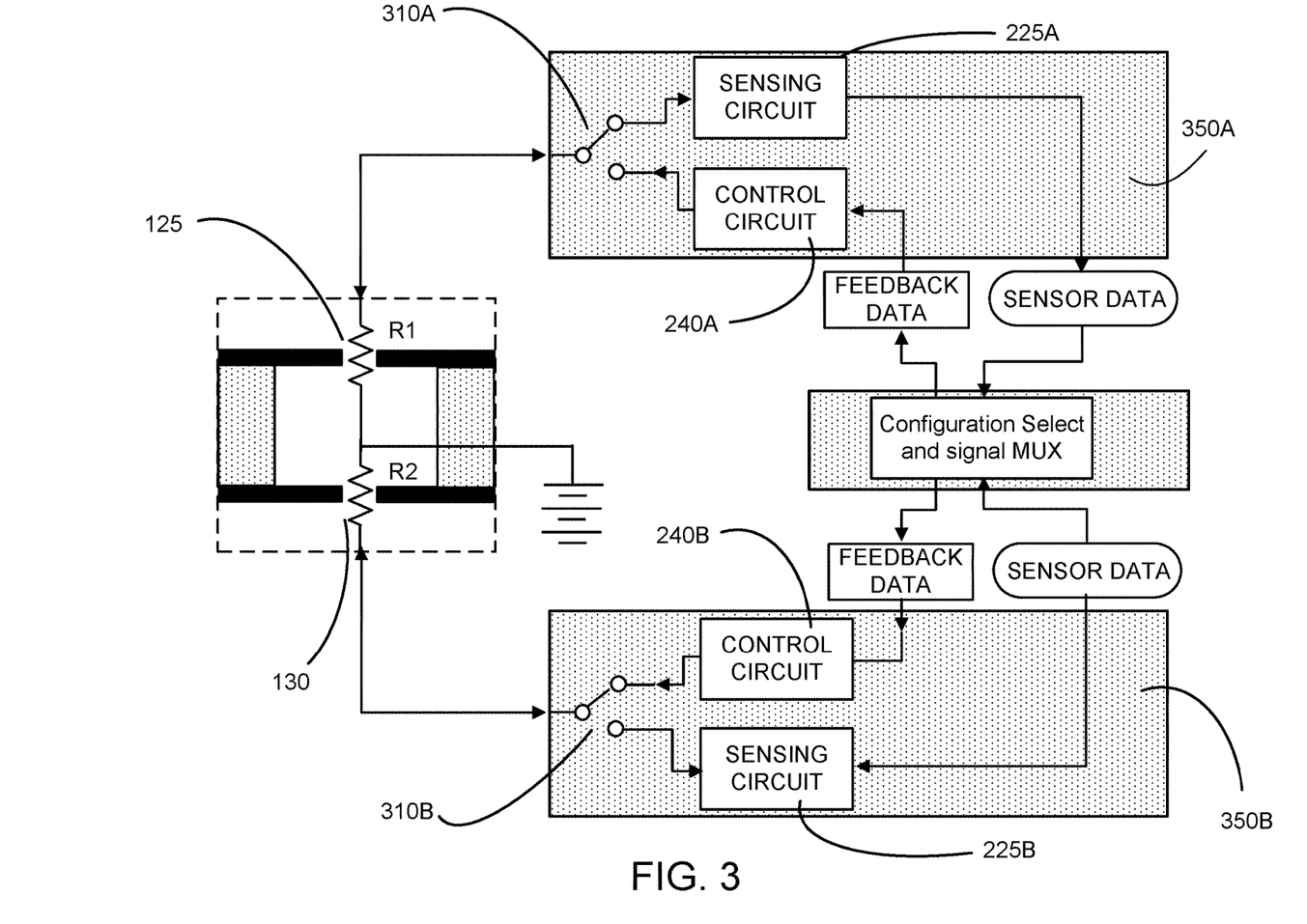
FIG. 3 depicts an example two nanopore device with a sensing circuitry and a control circuitry option for each pore, and a switch between the two options for each pore, in accordance with one embodiment.

In various embodiments, the sensor and control circuitry options are available at each of the two-pores. FIG. 3 depicts an example two nanopore device with a sensing circuitry 225 and a control circuitry 240 option for each nanopore, and a switch 310 between the two options for each pore, in accordance with one embodiment. In particular, a first nanopore 125 is incorporated in a first overall circuitry 350A that includes a first set of both a sensing circuitry 225A and a control circuitry 240A. Additionally, a second nanopore 130 is incorporated in a second overall circuitry 350B that includes a second set of both a sensing circuitry 225B and a control circuitry 240B. Each overall circuitry 350 includes a switch 310A and 310B that enables switching between a sensing circuitry 225 and control circuitry 240 of each overall circuitry 350. In one embodiment, setting each switch 310 can enable sensing across the first nanopore 125 and control at a second nanopore 130, or vice versa. In various embodiments, the switches 310A and 310B may be embodied differently than displayed in FIG. 3. For example, certain hardware components may be shared between the sensing circuitry 225 and control circuitry 240 and therefore, each switch 310 can be configured such that the function of each circuitry (including the requisite hardware components) is appropriately enabled when desired. These embodiments are described in further detail below in FIG. 4A and FIG. 4B.

In these embodiments, each of the first nanopore 125 and second nanopore 130 can be incorporated in an overall circuitry 350 with a dual role of 1) applying dynamic voltages to control movement of molecules and 2) detecting ionic measurements corresponding to translocation events across the nanopore. The switch 310A and 310B of each overall circuitry 350 is used to set the role of each overall circuitry 350A and 350B.

As shown in FIG. 3, each sensing circuitry 225 can provide sensor data whereas each control circuitry 240 receives feedback data. The sensor data from each sensing circuitry 225 can be received and processed by a configuration select and signal multiplexer. In various embodiments, the multiplexer can receive and filter the sensor data from each sensing circuitry 225. For example, the multiplexer filters out noise from each sensor data. The multiplexer directs the sensor data as feedback data to the opposite overall circuitry 350. For example, if the sensor data is generated by a sensing circuitry 225A of the first overall circuitry 350A, then the multiplexer directs the sensor data as feedback data to the control circuitry 240B of the second overall circuitry 350B.

Figure 4A:
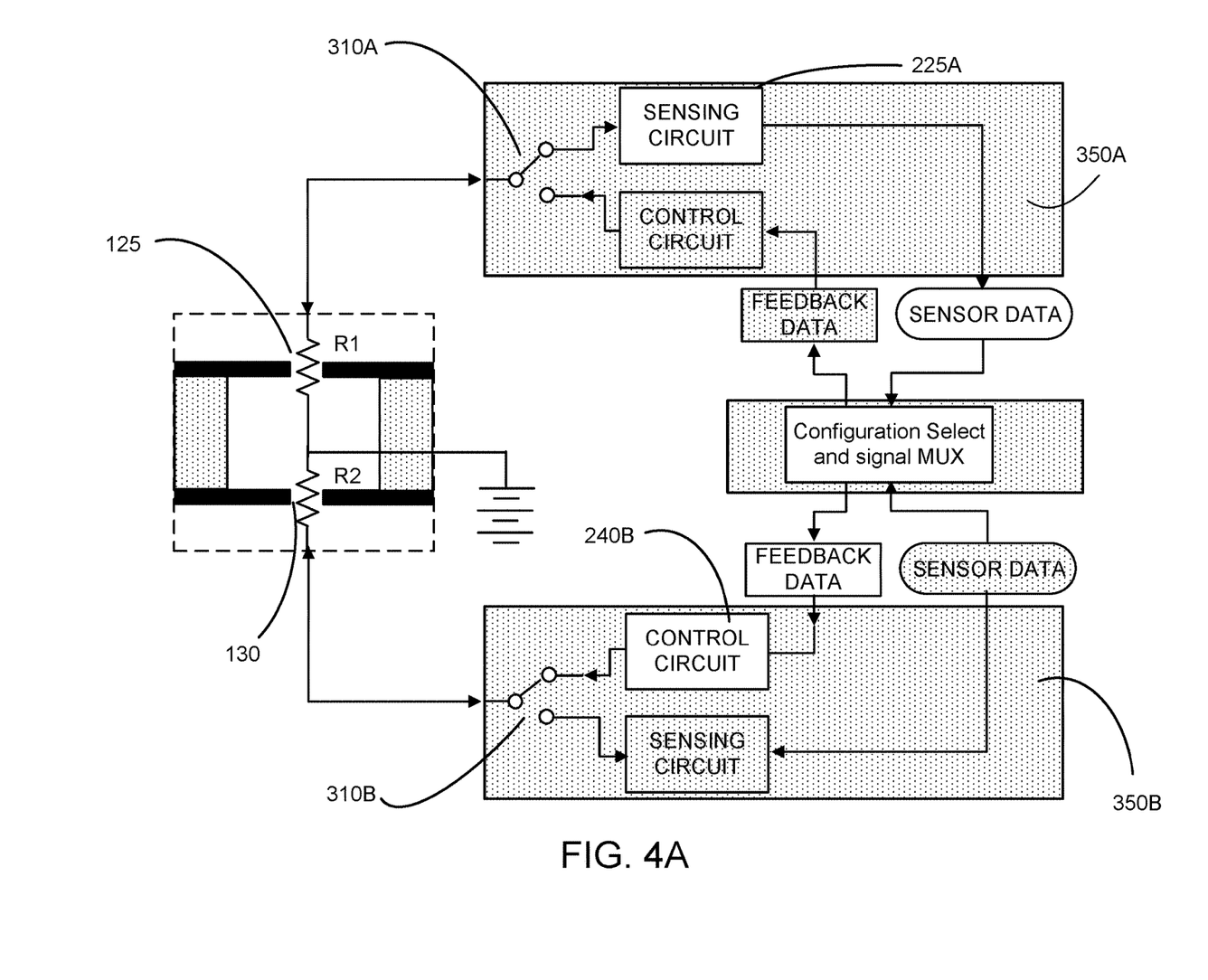
FIG. 4A depicts an example two nanopore device in a first configuration, in accordance with one embodiment.
Figure 4B:
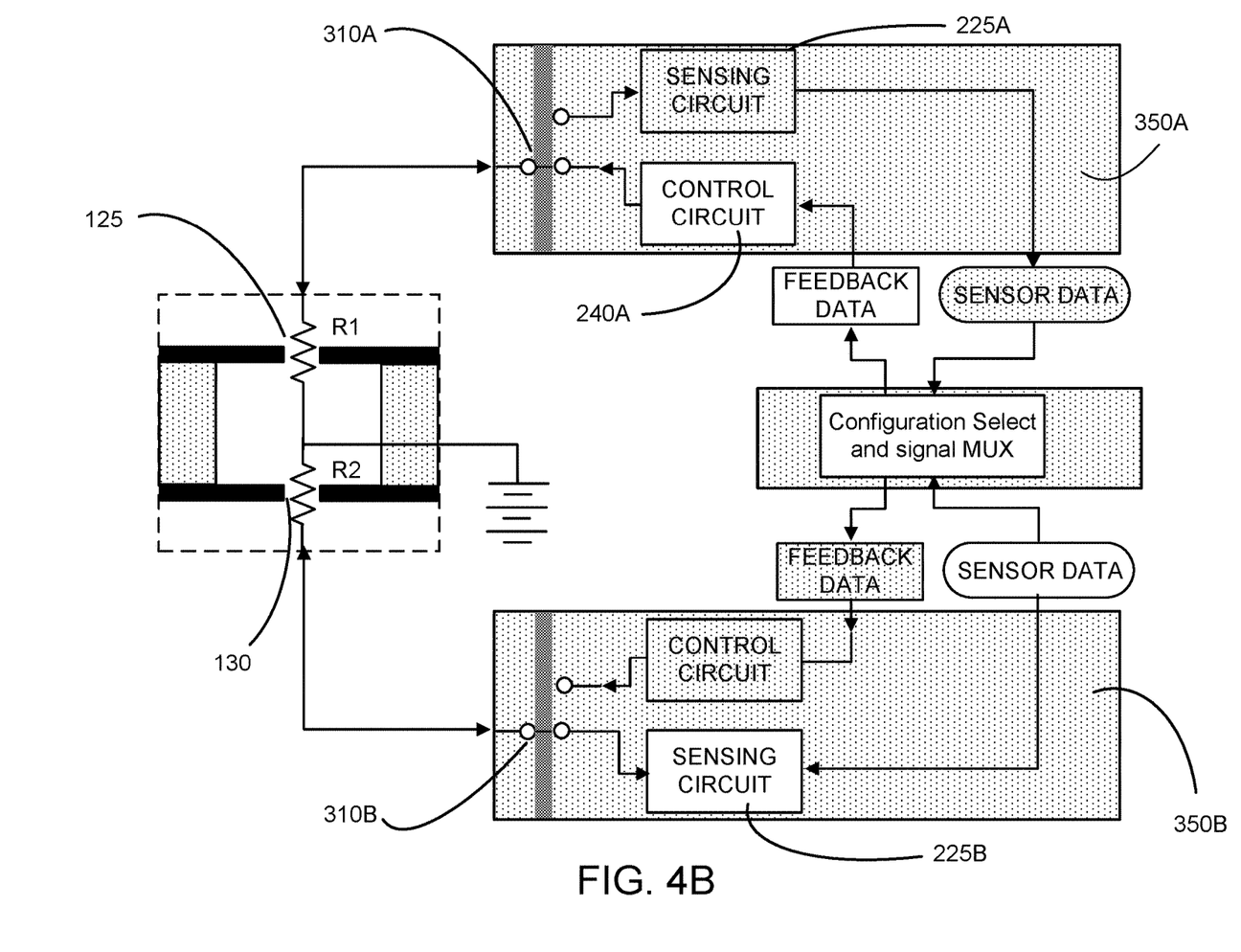
FIG. 4B depicts an example two nanopore device in a second configuration, in accordance with one embodiment.

Reference is now made to FIGS. 4A and 4B, which depict an example two nanopore device in a first and second configuration, respectively, in accordance with one embodiment. In the first and second configurations, the switches 310 control the connectivity to one sensing circuitry 225 and one control circuitry 240. In particular, the closed circuitries (and corresponding sensor data and feedback data) are shown in white boxes whereas the unconnected circuitries (e.g., open circuit) and the corresponding sensor data and feedback data are depicted in shaded boxes.

Referring to FIG. 4A, the first configuration of the two nanopore device refers to a first switch 310A connecting the sensing circuitry 225A of the first overall circuitry 350A and a second switch 310B connecting the control circuitry 240B of the second overall circuitry 350B. Therefore, the sensing circuitry 225A of the first overall circuitry 350A is used to detect the translocation of the molecule through the first nanopore 125. Additionally, the control circuitry 240B of the second overall circuitry 350B is used to control the motion of the molecule.

Referring to FIG. 4B, the second configuration of the two nanopore device refers to a first switch 310A connecting to the control circuitry 240A of the first overall circuitry 350A and a second switch 310B connecting the sensing circuitry 225B of the second overall circuitry 350B. Therefore, the control circuitry 240A of the first overall circuitry 350A is used to control the motion of the molecule whereas the sensing circuitry of the second overall circuitry 350B is used to detect the translocation of the molecule through the second nanopore 130.

In various embodiments, the two nanopore device may be placed in additional configurations. For example, a third configuration includes connecting both sensing circuitries 225A and 225B through switches 310A and 310B, respectively. Therefore, the static voltages applied by the sensing circuitries 225A and 225B across their respective nanopores 125 and 130 can be used to draw a molecule through one of the nanopores into the middle chamber 110 or into the channel 150 located between the two nanopores. In various embodiments, the third configuration of the two nanopore device is implemented after a molecule is initially loaded into a chamber (e.g., a first chamber 105) of the two nanopore device.

As another example, an additional configuration includes connecting both control circuitries 240A and 240B through switches 310A and 310B, respectively. This configuration can be utilized in conjunction with an additional method of sensing molecule translocation through a nanopore. As an example, an optical auxiliary sensor can be implemented to optically image molecules that may be optically tagged. Therefore, the two control circuitries 240A and 240B of the additional configuration can enable finer control over molecule motion through one or both nanopores.

Operation of Two-pore, One Sensor

Generally, a control circuitry 240 and a sensor circuitry 225, as shown in FIG. 2A/2B, or multiple control circuitries 240A/240B and multiple sensor circuitries 225A/225B, as shown in FIG. 3/4A/4B can be employed together in a two-pore one sensor device to control the movement of a molecule, such as a DNA segment, for sensing and data collection. Although the subsequent description refers to the two nanopore device in a second configuration state (e.g., sensing circuitry 225B incorporating the second nanopore 130 and control circuitry 240A incorporating the first nanopore 125), the description can similarly be applied to additional configuration states (e.g., first configuration state).

For example, in the two-pore device depicted in FIGS. 2A and 2B, the control circuitry 240 applies a dynamically altered voltage across the first nanopore 125 that generates a force that directionally opposes the force generated by the static voltage applied across second nanopore 130 by the sensor circuitry 225, with a dynamic magnitude that results in controlled motion of the molecule in either direction. In particular, the voltage applied by the control circuitry 240 across the first nanopore 125 can direct the movement of molecules by generating varying field force strengths that are in magnitude larger than, equal to, or less than the static force deriving from the voltage applied to the second nanopore 130 by the sensor circuitry 225. Therefore, dynamic adjustment of the voltage field force at the first nanopore 125, relative to the static field force at the second nanopore 130, enables control over the net direction of motion of a molecule as well as the rate of motion (e.g., velocity) of a molecule situated between both nanopores 125 and 130 in either the middle chamber 110 or channel 150.

In a related example, in the two-pore device depicted in FIGS. 2A and 2B, the control circuitry 240 applies a driving force using an AC electric field with an associated AC frequency. Control or selection of the AC frequency (or another aspect of the AC electric field applying the driving force) can be based upon information from the sensor circuitry 225. For instance, one or more of frequency (e.g., frequency at which a target passes back and forth through a nanopore), amplitude of a signal, phase of a signal, event duration (e.g., associated with target motion at a pore), quantity of targets, and/or any other suitable feature of an electrical signal from the sensor circuitry 225 can be used to dynamically adjust aspects of the AC electric field applying the driving force of the control circuitry 240. Therefore, a driving force from an AC source at one nanopore (e.g., the second nanopore 130) can enable control over the net direction of motion of a molecule as well as the rate of motion (e.g., velocity) of a molecule situated between nanopores 125, 130.

In particular, the dynamic voltage applied by the control circuitry 240 can have a phase that is shifted in comparison to the phase of the sensor data gathered by the sensor circuitry 225. Therefore, as the molecule passes through the second nanopore 130 in a first direction, the applied dynamic voltage changes such that the force imparted by the dynamic voltage opposes the direction of movement of the molecule.

The molecule then changes directions and passes through the second nanopore 130 in a second direction (e.g., opposite of the first direction). Here, the dynamic voltage changes again to oppose the second direction of movement of the molecule. This process can be repeated to enable the molecule to pass back and forth through the second nanopore 130 until a sufficient measurement of the segment of the molecule is obtained.

By oscillating the less-than or greater-than force at the first nanopore 125, relative to the static force at the second nanopore 130, the segments of the molecule can be sensed many times by the sensor circuitry 225B by repeatedly passing the molecule through the second nanopore 130. Doing so can improve the signal of detected ionic changes corresponding to translocation of the molecule across the second nanopore 130 which is useful for a variety of signal processing purposes, e.g., to improve sequencing of a molecule such as DNA. The repeated back and forth passing of the molecule, such as a polynucleotide, through the second nanopore 130 is referred to as "flossing" of the polynucleotide. Specifically, the flossing of the DNA segment (or a portion of the DNA segment) through the second nanopore 130 is in response to applied forces (e.g., electrical forces derived from the applied voltages) and can further include frequency data corresponding to the rate of translocation of the DNA segment through the second nanopore 130. As an example, the frequency data is the period of a single nucleotide base that begins at an initial position, translocates across the second nanopore 130 in a first direction (e.g., enter into middle chamber 110 or leave middle chamber 110), translocates back across the second nanopore 130 in a direction opposite to the first direction, and returns to the initial position.

Figure 5:
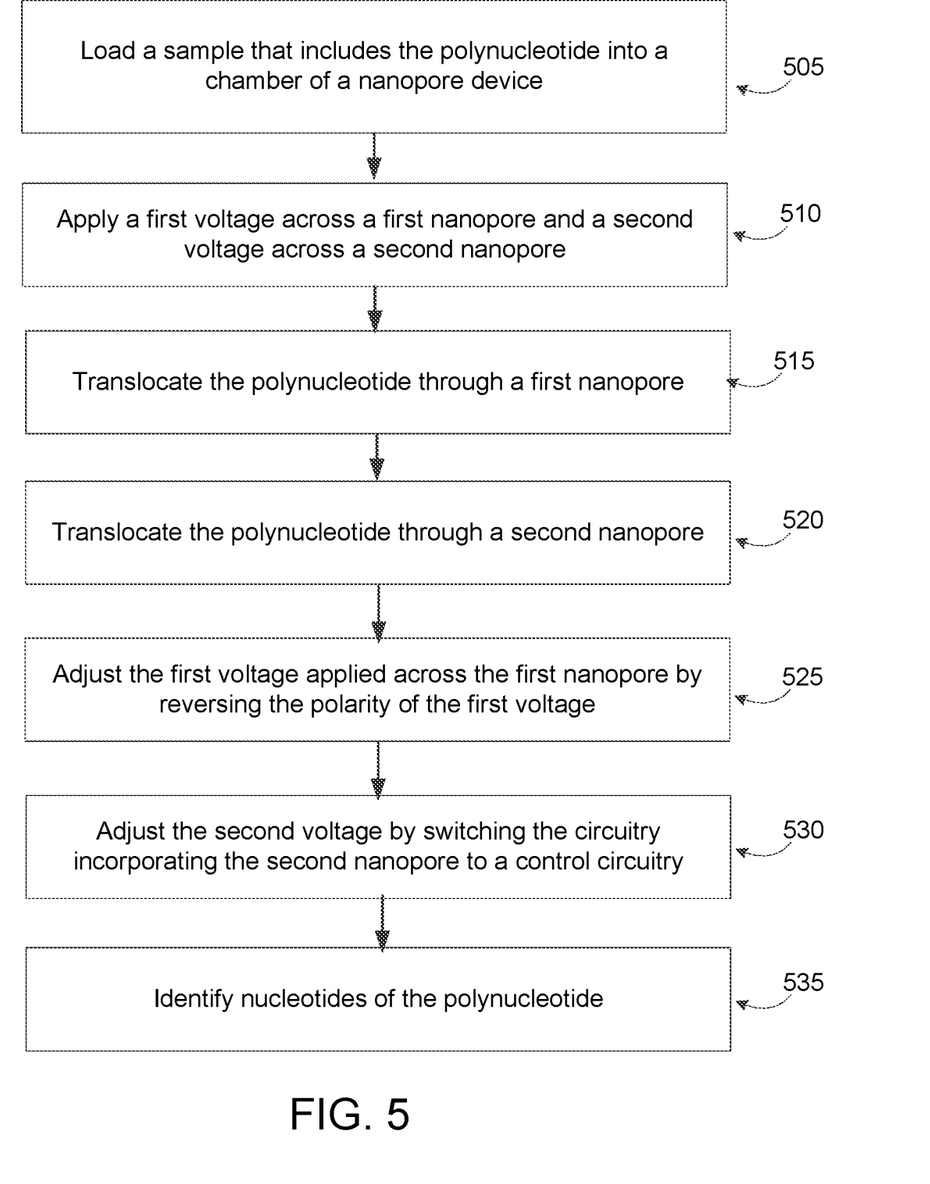
FIG. 5 depicts a flow process for sequencing a molecule such as a polynucleotide, in accordance with an embodiment.

FIG. 5 depicts a flow process for sequencing a molecule such as a polynucleotide, in accordance with an embodiment. Specifically, a sample that includes the polynucleotide is loaded 505 into a first chamber 105 of a nanopore device 100. In some embodiments, the polynucleotide can be loaded into a different chamber (e.g., third chamber 115 as shown in FIG. 2A or second chamber 110 in FIG. 2B). The two nanopore device applies 510 a first voltage across a first nanopore 125 and a second voltage across a second nanopore 130. In various embodiments, this can be accomplished by placing the two nanopore device in a third configuration state (e.g., both the first nanopore 125 and second nanopore 130 are incorporated in sensing circuitries 225A and 225B, respectively). Therefore, the first and second voltages are each applied by a sensing circuitry 225. The polynucleotide translocates 515 from the first chamber 105 and through a first nanopore 125. Specifically, the sensor circuitry 225A of the first nanopore 125 can apply a constant voltage across the first nanopore 125 that generates an electrical force that draws the polynucleotide through the first nanopore 125. The sensor circuitry 225 may be configured to measure changes in ionic current through the first nanopore 125. Therefore, when the polynucleotide translocates through the first nanopore 125, the sensor circuitry detects the translocation event based on a detected change in ionic current. Additionally, the polynucleotide translocates 520 through the second nanopore 130 due to the applied voltage by the sensor circuitry 225B.

The two nanopore device may switch into a different configuration that opposes the direction of the movement of the molecule. For example, the two nanopore device switches from a third configuration state to a first configuration state or a second configuration state depending on the directional movement of the molecule. If the molecule was initially loaded into the first chamber 105, then the molecule is directionally exiting from the first chamber 105 and moving towards the second 110 or third chamber 115. Therefore, to oppose the movement of the molecule, the two nanopore device can switch from a third configuration into a first configuration state (e.g., see FIG. 4A). In some embodiments, if the molecule was initially loaded into a bottom chamber (e.g., third chamber 115 in FIG. 2A or second chamber 110 in FIG. 2B), then the molecule is directionally moving towards the first chamber 105. Therefore, to oppose the movement of the molecule, the two nanopore device can switch from a third configuration into a second configuration state (e.g., see FIG. 4B).

The subsequent description refers to switching the two nanopore device to a first configuration state, but can also be applied for a switch to the second configuration state. In various embodiments, the first voltage applied by the circuitry incorporating the first nanopore 125 is adjusted 525. Specifically, the polarity of the sensing circuitry 225A is set such that it opposes the movement of the molecule. For example, the polarity of sensing circuitry 225A can be reversed from a first polarity in the third configuration state to a reverse of the first polarity in the first configuration state. Additionally, the second voltage applied by the circuitry incorporating the second nanopore 130 is also adjusted 530. Specifically, the control circuitry 240B of the second overall circuitry 350B applies 320 an adjusted second voltage across the second nanopore 130 in response to detecting that the polynucleotide has translocated through the first nanopore 125. Generally, the magnitude of the adjusted second voltage applied by the control circuitry 240 is dynamically changing (e.g., an oscillating voltage) such that the electrical force arising due to the adjusted second voltage can oppose the static force arising from the adjusted first voltage. The second voltage applied by the control circuitry 240 has a particular waveform (e.g., varying amplitude/magnitude at a particular frequency) such that the polynucleotide can similarly oscillate (e.g., floss) back and forth through the first nanopore 125. As the polynucleotide oscillates, the sensor circuitry 225A can detect ionic current changes through the first nanopore 125 that corresponds to the translocation of nucleotide bases of the polynucleotide. Each nucleotide base can be read multiple times as the polynucleotide flosses back and forth through the first nanopore 125, thereby enabling the more accurate identification 535 of individual nucleotides of the polynucleotide.

When a single nucleotide base from the polynucleotide has been sufficiently read, a polynucleotide exit state in the applied second voltage can be applied by the control circuitry 240B to allow for DNA segment incrementation. In other words, the second voltage can be temporarily adjusted to allow a subsequent nucleotide base pair to translocate through the first nanopore 125, at which point the second voltage can be resumed to floss the subsequent nucleotide base pair back and forth through the first nanopore 125. The magnitude and frequency of the applied second voltage across the second nanopore 130 by the control circuitry 240B can be tailored according to frequency information corresponding to the ionic current measurements detected by the sensor circuitry 225A.

In various embodiments, an automated and functional circuitry (e.g., using state machine or machine learning algorithms in concert with feedback control) could control both the sensor circuitry 225A and the control circuitry 240B, to continuously monitor the sensed data. Therefore, a section of DNA can be read for optimal performance. For example, if the ion current corresponding to a DNA translocation event through the first nanopore 125 is not resolved, then the control circuitry 240 can perform a step-wise increase in the applied voltage across the second nanopore 130. Doing so increases the force opposing the static force applied by the sensor circuitry 225, thereby slowing the movement of a DNA segment as it translocates through the first nanopore 125. This improves the signal to noise ratio for each DNA translocation across the first nanopore 125 until the desired performance (e.g., signal resolution) is achieved.

Flossing a DNA segment and sensing the segment multiple times using a sensing circuitry enables the reduction of signal error to an acceptable level. Alignment of signals can be used to achieve consensus sequences with acceptable accuracy. In some embodiments, the multiple reads corresponding to multiple DNA translocations can be used to generate a consensus signal, which can subsequently be used to identify the nucleotide base pair.

Additional Considerations

While embodiments, variations, and examples of two-pore devices and methods implemented with two-pore devices are described above, alternative embodiments, variations, and examples of the invention(s) described can involve a non-two-pore device. For instance, in variations, second chamber 110 (and variations described thereof) can be a conductive channel of a single pore device, wherein the single pore device has control circuitry (e.g., by way of gate voltage), sensing circuitry (e.g., in relation to source-to-drain current flow), with the ability to switch between control circuitry and sensing circuitry. Such a single pore device can be manufactured with a lithography process, a drilling process, or any other suitable process that generates a channel or chamber through layers of material.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A two-pore device comprising:
   an upper chamber, a middle chamber and a lower chamber, wherein the upper chamber is in communication with the middle chamber through a first nanopore, and wherein the middle chamber is in communication with the lower chamber through a second nanopore,
   a sensing circuitry, a control circuitry, and a switch controlling connectivity to the sensing circuitry and the control circuitry for each of the first nanopore and second nanopore,
      each sensing circuitry configured to, when connected to the corresponding switch, apply a constant voltage across the corresponding nanopore and further configured to measure sensing current through the corresponding nanopore,
      each control circuitry configured to, when connected to the corresponding switch, apply a dynamic voltage across the corresponding nanopore, the applied dynamic voltage determining a controlled motion of a charged polymer across the first nanopore and the second nanopore, wherein the applied dynamic voltage is applied using a direct current-biased alternating current signal source, and
   wherein the sensing current is derived from the charged polymer during the controlled motion.

2. The two-pore device of claim 1, wherein each sensor circuitry comprises a transimpedance amplifier.

3. The two-pore device of claim 2, wherein the transimpedance amplifier is one of a patch clamp or voltage clamp amplifier.

4. The two-pore device of any one of claim 1, wherein each control circuitry comprises a phase lock loop (PLL).

5. The two-pore device of claim 4, wherein the control circuitry of the first nanopore is configured to generate an oscillatory voltage output based feedback from the sensor circuitry of the second nanopore.

6. The two-pore device of claim 5, wherein a phase difference between a frequency of the oscillatory voltage output and the frequency of the sensing current is fixed over time.

7. The two-pore device of claim 5, wherein the oscillatory voltage output is provided to a voltage-controlled amplifier (VCA) that applies the dynamic voltage across the second nanopore.

8. The two-pore device of claim 1, wherein the middle chamber is electrically coupled as an electrical return path for both the sensor circuitry and the control circuitry of at least one of the first nanopore or second nanopore.

9. The system of claim 1, comprising a first operation mode in which the switch of the first nanopore is connected to the sensing circuitry of the first nanopore and the switch of the second nanopore is connected to the sensing circuitry of the second nanopore.

10. A two-pore device comprising:
    an upper chamber and a lower chamber, wherein the upper chamber is in communication with the lower chamber through a first nanopore and a second nanopore,
    a sensing circuitry a control circuitry, and a switch controlling connectivity to the sensing circuitry and the control circuitry for each of the first nanopore and second nanopore,
       each sensing circuitry, when connected to the corresponding switch associated with the corresponding nanopore, configured to apply a constant voltage across the corresponding nanopore and further configured to measure sensing current through the corresponding nanopore,
       each control circuitry, when connected to the corresponding switch associated with the corresponding nanopore, configured to apply a dynamic voltage across the corresponding nanopore, the applied dynamic voltage determining a controlled motion of a charged polymer across the first nanopore and the second nanopore, wherein the applied dynamic voltage is applied using a direct current-biased alternating current signal source, and
    wherein the sensing current is derived from the charged polymer during the controlled motion.

11. The two-pore device of claim 10, wherein the device further comprises a first membrane layer that includes the first nanopore, a second membrane layer that includes the second nanopore, and a conductive middle layer between the first membrane and second membrane layer.

12. The two-pore device of claim 11, wherein the conductive middle layer is electrically coupled as an electrical return path for both the sensor circuitry and the control circuitry of at least one of the first nanopore or second nanopore.

13. A method for sequencing a polynucleotide, the method comprising:
    loading a sample comprising the polynucleotide in a first chamber of a nanopore device;

translocating the polynucleotide through a first nanopore by using a sensing circuit of the first nanopore to apply a first voltage across the first nanopore;

translocating the polynucleotide through a second nanopore by using a sensing circuit of the second nanopore to apply a second voltage across the second nanopore;

adjusting the first voltage applied across the first nanopore by reversing a polarity of the first voltage applied by the sensing circuit of the first nanopore;

adjusting the second voltage across the second nanopore by disconnecting a switch associated with the second nanopore from the sensing circuit of the second nanopore and connecting the switch to a control circuit of the second nanopore, wherein the adjusted second voltage generates an electrical force that opposes an electrical force generated by the adjusted first voltage, and wherein the adjusted second voltage is applied using a direct current-biased alternating current signal source; and identifying nucleotides of the polynucleotide.

14. The method of claim 13, wherein the adjusted second voltage is an oscillating control circuit voltage and wherein identifying nucleotides of the polynucleotide comprises:

for an initial oscillation of the applied oscillating voltage, detecting a first change in ionic current across the first nanopore corresponding to a first translocation of a nucleotide of the polynucleotide; and for a subsequent oscillation of the applied oscillating voltage, detecting a second change in ionic current across the first nanopore corresponding to a second translocation of the nucleotide of the polynucleotide.

15. The method of claim 14, wherein the adjusted second voltage is applied based on a feedback signal captured by the sensing circuit of the first nanopore.

16. The method of claim 15, wherein the feedback signal is a current measured across the first nanopore, the current being a measure of polynucleotide movement across the first nanopore.

17. The method of claim 16, wherein the measure of polynucleotide movement is a measure of one of polynucleotide position, velocity, or acceleration.

18. The method of claim 15, wherein the feedback signal is designed in either a frequency domain or a time domain by using one of feedforward or feedback.

19. The method of claim 15, wherein the feedback signal is designed using an estimator and filter that are co-designed to estimate molecule-induced changes in current.

20. The method of claim 13, wherein the adjusted second voltage is applied with a frequency range between 0.001 Hz and 100 MHz and an amplitude range between 0.001 mV and 10 V.

* * * * *

UNITED STATES PATENT AND TRADEMARK OFFICE
CERTIFICATE OF CORRECTION

PATENT NO. : 11,099,169 B2
APPLICATION NO. : 16/009007
DATED : August 24, 2021
INVENTOR(S) : Stamm et al.

Page 1 of 1

It is certified that error appears in the above-identified patent and that said Letters Patent is hereby corrected as shown below:

In the Claims

In Column 14, in Claim 4, Line 4, after "device of" delete "any one of".

In Column 14, in Claim 9, Line 23, delete "system" and insert -- two-pore device --.

In Column 14, in Claim 10, Line 33, after "sensing circuitry" insert -- , --.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*